United States Patent
Dauster et al.

(10) Patent No.: US 9,005,260 B2
(45) Date of Patent: Apr. 14, 2015

(54) RECEIVER BODY FOR SPINAL FIXATION SYSTEM

(75) Inventors: Andrew Dauster, Breinigsville, PA (US); Matthew Kovach, Steamboat Springs, CO (US); Paul Weaver, Douglassville, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 1403 days.

(21) Appl. No.: 12/321,099

(22) Filed: Jan. 15, 2009

(65) Prior Publication Data

US 2010/0179602 A1 Jul. 15, 2010

(51) Int. Cl.
*A61B 17/04* (2006.01)
*A61B 17/70* (2006.01)

(52) U.S. Cl.
CPC ......... *A61B 17/7032* (2013.01); *A61B 17/7086* (2013.01)

(58) Field of Classification Search
CPC ...................................................... A61B 17/04
USPC ........... 606/99, 246, 250, 256, 260, 264, 266, 606/270, 274, 914
See application file for complete search history.

(56) References Cited

U.S. PATENT DOCUMENTS

| | | | |
|---|---|---|---|
| 6,540,748 B2 | 4/2003 | Lombardo | |
| 2003/0225408 A1 | 12/2003 | Nichols et al. | |
| 2004/0162560 A1 | 8/2004 | Raynor et al. | |
| 2004/0193160 A1 | 9/2004 | Richelsoph | |
| 2004/0254576 A1 | 12/2004 | Dunbar et al. | |
| 2006/0025768 A1 | 2/2006 | Iott et al. | |
| 2006/0235393 A1* | 10/2006 | Bono et al. | 606/61 |
| 2007/0167949 A1 | 7/2007 | Altarac et al. | |
| 2007/0270830 A1 | 11/2007 | Morrison | |

OTHER PUBLICATIONS

European Search Report for European Application No. EP 10 15 0805, dated Mar. 10, 2010.
Office Action for European Application No. EP 10 15 0805.9 dated Jun. 8, 2010.

* cited by examiner

*Primary Examiner* — Thomas J Sweet
*Assistant Examiner* — Matthew Schall
(74) *Attorney, Agent, or Firm* — RatnerPrestia

(57) ABSTRACT

A receiver body for an elongated spinal fixation element includes a housing portion with one or more flanges extending outwardly. In one embodiment, the receiver body includes first and second flanges extending outwardly from the housing portion. The housing portion includes first and second slots that form a passage through the housing portion. Each flange has a circular perimeter edge and a chamfered section, the chamfered section having a notched undercut for engagement with an instrument. In another embodiment, the receiver body includes a housing portion having a circular flange with a first chamfered section and a second chamfered section diametrically opposite the first chamfered section. The first chamfered section has a first aperture that opens out beneath the flange, and the second chamfered section has a second aperture that opens out beneath the flange. The first and second apertures form diametrically opposed pivot-attachment points for an instrument.

23 Claims, 8 Drawing Sheets

RECEIVER BODY FOR SPINAL FIXATION SYSTEM

FIELD OF THE INVENTION

The present invention relates generally to spinal fixation systems, and more specifically to components for fixing an elongated spinal fixation member, such as rod, to a bone fastener.

BACKGROUND OF THE INVENTION

A number of spinal fixation systems feature a fixation rod that is anchored by two or more bone screws. To interconnect the fixation rod with the bone screws, each bone screw incorporates some form of cap or "receiver body" that is either integral with the screw, or surrounds a head portion on the screw. The receiver bodies include some form of opening, such as an open channel, to receive the fixation rod. Surgeons must apply a significant amount of force to advance or reduce a fixation rod into a proper position in the receiver body. In addition, surgeons must apply a significant amount of force to securely fix the rod in the channel within the receiver body. These forces result in various stresses on the receiver body.

SUMMARY OF THE INVENTION

In a first aspect of the invention, a receiver body for an elongated spinal fixation element includes a housing portion, with first and second flanges extending outwardly from the housing portion. The housing portion includes a first slot and a second slot opposite the first slot, the first and second slots forming a passage through the housing portion. The first flange has a circular perimeter edge and a chamfered section, the chamfered section having a notch for engagement with an instrument. The second flange also has a circular perimeter edge and a chamfered section, the chamfered section having a notch for engagement with an instrument. The notch of the second flange is positioned diametrically opposite the notch of the first flange.

In a second aspect of the invention, a receiver body for an elongated spinal fixation element includes a housing portion having a circular flange extending radially outwardly from the housing portion. The circular flange includes a first chamfered section and a second chamfered section diametrically opposite the first chamfered section. The first chamfered section has a first aperture that opens out beneath the flange, and the second chamfered section has a second aperture that opens out beneath the flange. The first and second apertures form diametrically opposed pivot-attachment points for an instrument.

BRIEF DESCRIPTION OF THE DRAWINGS

The foregoing summary and the following description will be better understood in conjunction with exemplary illustrations that are provided in the accompanying drawing figures, of which.

DETAILED DESCRIPTION OF EMBODIMENTS OF THE INVENTION

Figure 1:
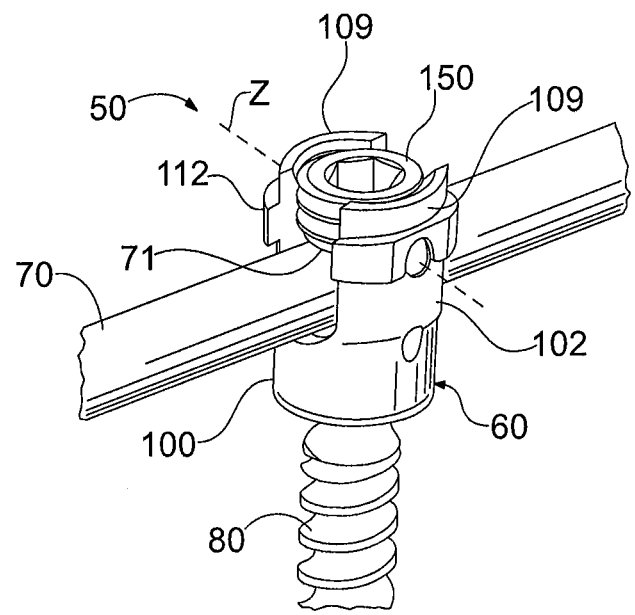
FIG. 1 is a perspective view of a spinal fixation construct, showing a rod receiver component in accordance with one exemplary embodiment of the invention, with elements of the construct truncated for clarity.

Although the invention is illustrated and described herein with reference to specific embodiments, the invention is not intended to be limited to the details shown. Rather, various modifications may be made in the details within the scope and range of equivalents of the claims and without departing from the invention, as will be understood from the examples described below.

Referring to the drawing figures generally, a number of examples of rod receiver bodies are shown in accordance with exemplary embodiments of the present invention. Receiver bodies in accordance with the invention utilize an external geometry to accomplish a number of important objectives. First, the external geometries allow for easy and secure attachment of a variety of instruments, including but not limited to rod persuader instruments. Second, the external geometries provide an optional pivot point for movable instruments or levers that pivot relative to the receiver body during operation. Third, the external geometries provide one or more surfaces for applying upward axial force on the receiver body, so as to assist in locking down a rod in the receiver body, for example, or to manipulate the position of vertebral body to which the implant is anchored. Fourth, the geometry provides a non-uniform distribution of wall thickness along the length of the receiver body, which provides for relative stiffening near the proximal end of the body, but not the distal end. This provides resistance to radial splaying near the proximal end of the receiver body, associated with the insertion of a fixing element, without impeding radial expansion at the bottom or distal end of the receiver body, associated with tightening a screw head against the interior of the receiver body. The walls of the receiver body, particularly at instrument attachment points, have pre-determined thicknesses that withstand shear forces created by internal locking mechanisms used in the receiver body. In embodiments that have a threaded internal surface to receive a threaded fixing element, such as a screw, the wall thicknesses at the instrument attachments points are thick enough to withstand shear forces from the maximum axial loading on the screw thread. These and other properties of the receiver bodies of the invention will be apparent from the specific example described below.

Figure 2:
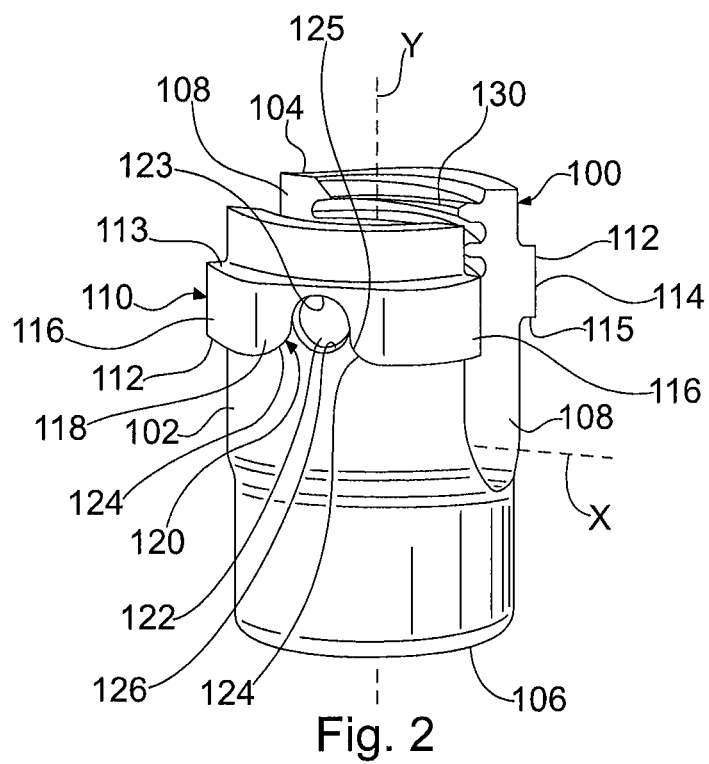
FIG. 2 is a perspective view showing the rod receiver of FIG. 1 in isolation.

Referring now to FIGS. 1 and 2, a rod fixation construct 50 is shown in accordance with one exemplary embodiment of the invention. Construct 50 features a screw implant 60 and a spinal fixation rod 70 anchored into the screw implant. Screw implant 60 includes a fastener in the form of a threaded bone screw 80, and a rod receiver 100, the latter sometimes referred to as a "receiver body" or "cap". Rod receiver 100 includes a housing portion 102 with an external geometry that provides a universal attachment or engagement feature for instrumentation. As will be explained, attachment or engagement features in accordance with the present invention are designed to cooperate with various instruments. In particular, each receiver body in accordance with the invention may have a single external geometry that cooperatively engages with an assortment of different instruments for different purposes.

Rod receiver components in accordance with the invention preferably have a cylindrical housing portion. The housing portion includes an instrument engagement section located on the exterior, closer to the proximal end of the body portion, and farther away from the distal end of the body portion. The terms "proximal" and "proximally", as used herein, refer to a location or direction oriented toward a surgeon, and away from the patient. In contrast, the terms "distal" and "distally", as used herein, refer to a location or direction oriented toward the patient, and away from the surgeon. By way of example, the proximal end of housing portion 102 in FIG. 2 is shown at 104, and the distal end of the housing portion is shown at 106.

Receiver body 100 includes an instrument engagement section 110 slightly offset from proximal end 102. In addition, receiver body 100 forms a pair of diametrically opposed rod-receiving slots 108 that extend parallel to one another. Slots 108 divide a section of housing portion 102 into two diametrically opposed tabs 109. Slots 108 also divide instrument engagement section 110 into two parts, with each part supported on one of the tabs. In particular, instrument engagement section 110 is divided into two flanges 112. Each flange 112 extends radially outwardly from a longitudinal receiver body axis Y running through housing portion 102, as shown. Each flange 112 includes a proximal edge 113 and a distal edge 115, one or both of which can be engaged by an instrument.

Flanges 112 are identical in configuration to one another, and are symmetrically arranged with respect to a longitudinal rod passage axis X. Each flange 112 has a peripheral outer edge 114 with a pair of circular segments 116. The outer edge 114 of each flange 112 further includes a chamfered or flat segment 118 located between circular segments 116, as shown. All four circular segments 116 have arc-shaped perimeter edges having equal radii from a point on axis Y and arranged relative to one another to define the outline of a cylinder, interrupted only by flat segments 118 and slots 108.

Flat segments 118 are diametrically opposed to one another on the exterior of the body, and may be formed by machining or other methods. Each flat segment 118 represents a face that exists inside the outline of the cylinder formed by circular segments 116, such that the flat segments do not extend radially outwardly from the center of housing portion 102 as far as the adjoining circular segments 116. Given the reduced dimension of receiver body 100 across flat segments 118, the flat segments provide telescopic access for instruments, as will be explained in further examples provided below.

Each flat segment 118 forms an attachment point that allows instruments to engage the receiver body 100. Referring to FIG. 2, flat segments 118 each include a notched undercut or "notch" 120, one of which is shown. The other notch that is not visible in FIG. 2 is located on the opposite side of housing portion 102, and has an identical configuration. Each notch 120 extends partially into its respective flange 118 and forms an engagement surface 122. In this arrangement, notches 120 open out beneath the flanges 112, but do not extend through the proximal edges of the flanges. Engagement surfaces 122 each have an inverted U-shape, including a central circular arc segment 123. A pair of rounded shoulder sections 124 join the central arc segment 123 with the distal edge 115 of flange 112.

Notches 120 are positioned directly opposite one another on the exterior of receiver body 100. An axis Z extending through the centers of notches 120 crosses through housing portion 102 perpendicularly with respect to the rod passage axis X. Each notch 120 includes a circular shallow bore 126 that is recessed into the wall of housing portion 102. Shallow bores 126 form engagement surfaces for pins or other types of male protuberances on instruments. It will be seen that shoulder sections 124 form a tapered mouth where distal edge connects with the notch. Shoulder sections 124 converge inwardly toward shallow bore 126 and merge with both the distal edge 115 of flange 112, and the arc-shaped section 123. The smooth transitions between the distal edges 115 and shoulders 124 form continuous guide ramps 125 to guide protuberances into the shallow bores. This allows surgeons to easily and properly connect instruments onto the receiver body, with no fiddling with the instruments.

FIG. 1 shows a rod construct in a fully locked-down condition. In this condition, the uppermost surface 71 of the rod 70, i.e. the section of the rod contacting set screw 150, is located beneath the notches 120 in flanges 112. That is, when rod 70 is fully seated in the rod receiver, the rod sits beneath the notch axis Z. By positioning the flanges 112 near proximal end 104, the flanges act as stiffeners to prevent radial splaying of the tabs 109 when set screw 150 is driven down into the receiver body. Radial deflection of receiver body 100 near proximal end 104 is not desirable, as it can cause the set screw to disengage from the threads in receiver body. Unlike proximal end 104, distal end 106 of receiver body 100 is not stiffened by thicker wall sections. This allows the distal end to deform somewhat when the rod is locked down, so that the distal end firmly engages the screw head.

As discussed above, the wall thickness of receiver body 100 is designed to withstand shear forces created when fixing elements, such as set screws, are driven into the receiver body. The depths of shallow bores 126 are pre-determined to provide enough wall material to withstand shear forces under maximum loading conditions, which may generate shear forces as large as 550 lbs. or larger.

Figure 3:
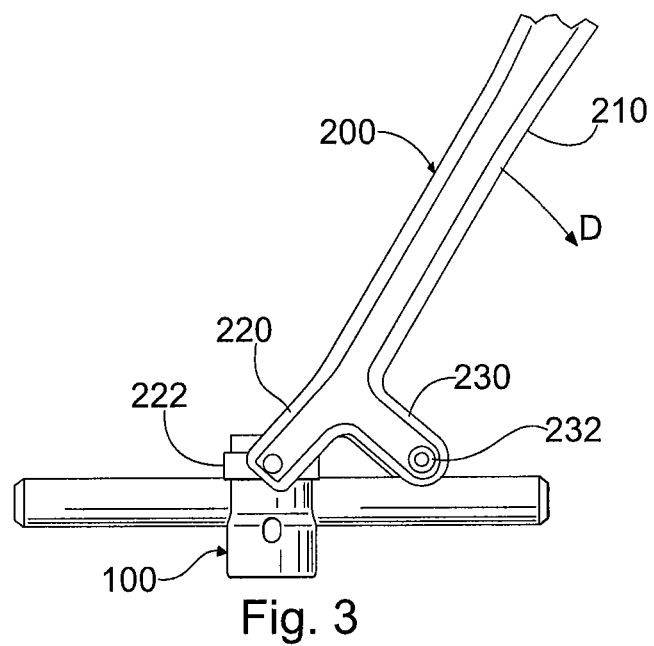
FIG. 3 is an elevation view of the rod receiver of FIG. 1 and a fixation rod being engaged by an instrument in accordance with the present invention, the instrument being truncated for clarity.
Figure 4:
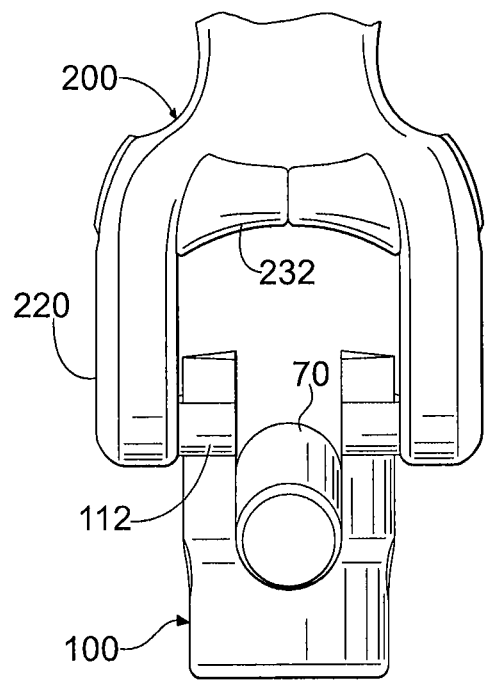
FIG. 4 is a perspective view of the rod receiver, rod and instrument of FIG. 3, with the instrument being truncated for clarity.

Referring now to FIGS. 3 and 4, receiver body 100 is shown engaged with one possible instrument configuration. Specifically, receiver body 100 is engaged with a rod reducer instrument 200 that acts a lever to pivot or "rock" a rod into a seated position in rod receiver body 100. Rod reducer instrument 200 has a lever portion 210, a first extension 220 and a second extension 230. First extension 220 has a pair of opposed pins 222 that connect with shallow bores 126 of receiver body. Shallow bores 126 retain the pins in a fixed axial position relative to receiver body 100, but permit instrument 200 to rotate in the shallow bores. Preferably, the diameter of shallow bores 126 is slightly larger than the diameter of the pins, so that the pins are free to pivot without frictional resistance and with minimal translation in the bores. When the pins on first extension 220 are pivotally supported in shallow bores 126, lever is operable to advance or reduce a rod into a desired axial position within the slots of receiver body. Second extension 230 includes a pusher bar 232 that engages the rod. Upon pivoting lever portion 210 downwardly, i.e. in the direction labeled "D", pusher bar 232 pivots through a downward arc and urges the rod downwardly into the slots of rod receiver body. In some cases, the rod may present some resistance to being held down in the receiver body. In such cases, a downward force can be maintained on lever portion 210 to hold down the rod in a seated position until a set screw, locking cap, or other fixing element can be inserted into the receiver body above the rod to hold the rod in place.

It will be important to note that the rod receiver bodies of the invention are not dependent on the type of fixing element used to secure a rod in place. Although the example shown in FIGS. 1 and 2 includes an internal thread 130 to receive a threaded set screw 150, rod receiver body need not be threaded, and may be internally configured to receive non-threaded fixing elements, including radially expandable locking caps, such as that shown in U.S. application Ser. No. 11/753,161 entitled "Pedicle Screw Fixation System", filed May 24, 2007 and assigned to the applicant, the contents of which are incorporated by reference herein in their entirety.

Figure 5:
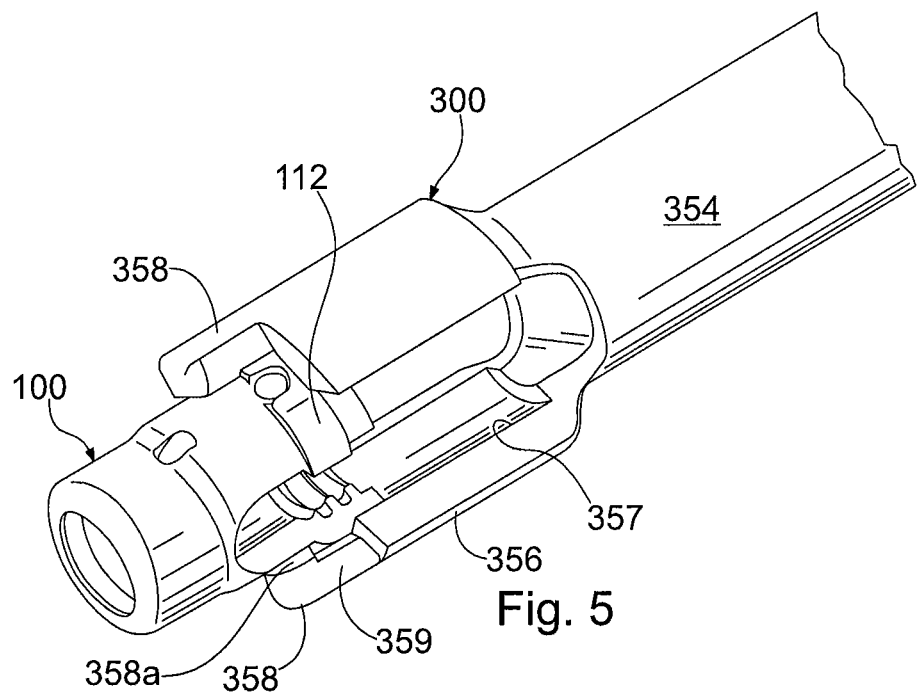
FIG. 5 is a perspective view of the rod receiver of FIG. 1 being engaged by another instrument in accordance with the present invention.

Referring now to FIG. 5, receiver body 100 is shown engaged with a second possible instrument configuration. Specifically, receiver body 100 is engaged with an instrument 300 that twists onto the flanges 112. Instrument 300 may be a rod introducer of the kind shown, for example, in U.S. application Ser. No. 11/753,161 referenced above, a down tube, or other instrument that is coupled to the receiver body by axial rotation. Instrument 300 includes an outer sleeve 354 with a socket end 356 adapted to engage proximal end 104 of receiver body 100. Socket end 356 is hollow, forming a generally cylindrical socket 357. The diameter of socket 357 is generally equal to or slightly larger than the diameter across the circular segments 116 of flanges 112. A pair of clamping tips 358 extend distally from socket end 356. Each clamping tip 358 has an inwardly facing surface that facilitates engagement with flanges 112. The distal edges 115 of flanges 112 form ledges that cooperatively engage clamping tips 358. Clamping tips 358 include inwardly-facing tabs 358a and recessed sections 359 adjacent to the tabs. The clearance or distance between tabs 358a is less than the diameter across circular segments 116, but greater than the dimension between flat segments 118. In this arrangement, clamping tips 358 are adapted to slide telescopically (i.e. slide axially) over flanges 112 when the clamping tips are radially aligned with flat portions 118. Once tabs 358a pass completely over flat surfaces 118, the tabs can be rotated beneath the circular segments 116 until the circular segments enter the recesses 359. Tabs 358a can be rotated beneath the circular segments 116 by twisting instrument 300. In this orientation, flanges 112 are captured between clamping tips to secure instrument 300 to receiver body 100.

Flanges 112 are symmetrical with respect to receiver body axis Y, providing an ambidextrous attachment means. That is, the provision of circular segments 116 on both sides of each flat segment 118 allow instruments such as instrument 300 to be twisted onto flanges 112 by either a clockwise rotation or a counterclockwise rotation. This accommodates surgeons who prefer to manipulate instruments with their left hand as well as those who prefer manipulating instruments with their right hand. In addition, the symmetrical flange arrangement allows instruments to be easily attached to the receiver body from any side. The required angular rotation or twisting angle is relatively small, requiring very little twisting motion. In the example shown, instrument 300 is twisted through an angle of about 22.5 degrees to lock the instrument onto the circular segments 116 of flanges 112. The relative dimensions of the circular and flat segments may be configured to permit instrument locking and unlocking to occur via other angles of rotation.

Instrument configurations like instrument 300 are operable to apply upward axial force, i.e. force in the proximal direction, on a receiver body. After clamping tabs 358a are rotated beneath circular segments 116, the tabs are radially aligned with the circular segments in a position to engage the distal edges 115 of flanges 112. By applying upward force on instrument 300, upward force is transferred to receiver body 100 through the engagement between the clamping tips 358 and flanges 112. This upward force may be used as an aid during rod insertion. Alternatively, upward force may be applied by a manipulation instrument to adjust the position of a vertebral body to which the implant is secured.

Figure 6:
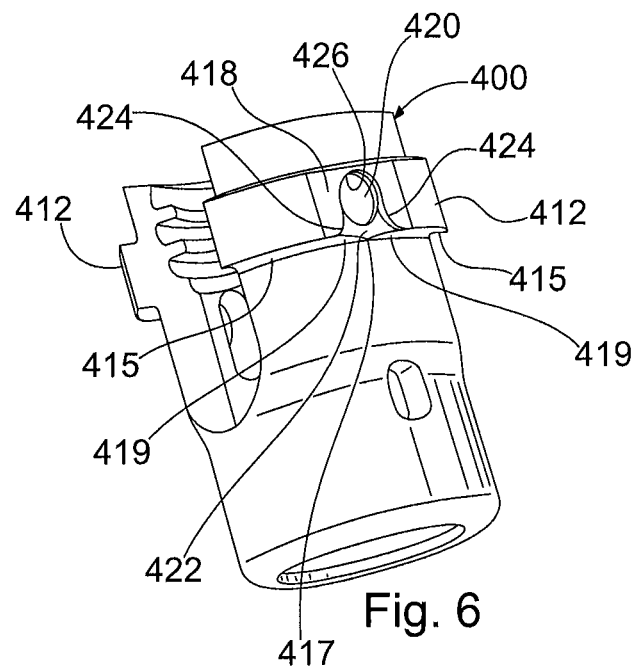
FIG. 6 is a perspective view of an alternate rod receiver in accordance with another exemplary embodiment of the present invention.

Referring now to FIG. 6, a receiver body 400 is shown in accordance with an alternate embodiment of the invention. Receiver body 400 includes a pair of flanges 412, with each flange 412 including a flat segment 418 and a notch 420, similar to receiver body 100. Notch 420 includes a flat apron area 422 and a shallow bore 426. Flat apron area 422 is recessed into flat segment 418, but the depth of the apron area is shallower than the depth of shallow bore 426. Flat areas of intermediate depth, like flat apron area 422, can assist in the machining process. For example, apron area 422 makes it easier to machine the rounded shoulder sections 424 of slot 420.

Flanges 412 each have a distal edge 415 that is contoured to facilitate the use of rod insertion instruments. More specifically, distal edge 415 is generally planar or flat beneath circular segments 416 of flange 412, but tapers distally to a small ridge 417 beneath apron area 422. The tapered section of distal edge 415 forms a pair of shoulders 419 symmetrically arranged on each side of ridge 417. Shoulders 419 are contoured to cooperate with rod instrumentation. For example, shoulders 419 can cooperate with pivoting lever rod persuaders, such as reducer instrument 200 described above, which have corresponding surfaces that mate with the shoulders. When used with pivoting instrumentation, shoulders 419 engage the corresponding surfaces inside the pivoting instruments when the instrument is pivoted or rocked through a certain angular motion relative to the receiver body. When one of the shoulders 419 contacts a corresponding surface in the instrument, the contacted shoulder acts as a stop that prevents further pivoting of the instrument. This feature can be used, for example, to limit the amount of axial force applied on the rod, or limit the depth to which the rod can be axially advanced in the receiver body.

Figure 7:
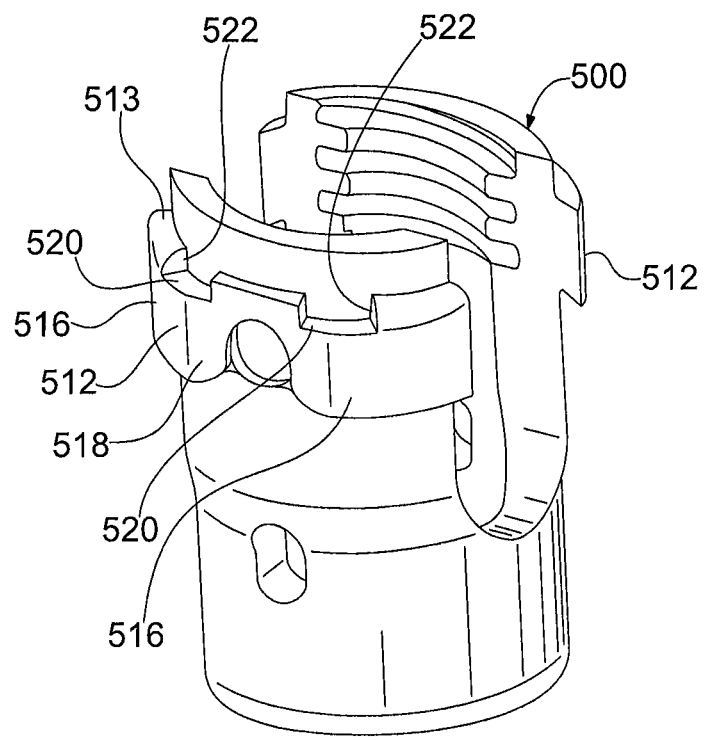
FIG. 7 is a perspective view of an alternate rod receiver in accordance with another exemplary embodiment of the present invention.

Referring now to FIGS. 7-10, additional receiver body embodiments are shown in accordance with exemplary embodiments of the invention. FIG. 7 shows a receiver body 500 with modified flanges 512. Each flange 512 includes two circular segments 516, a flat segment 518 between the circular segments, and a rounded proximal edge 513. Proximal edge 513 includes a pair of slots 520 positioned at transitions between circular segments 516 and flat segment 518. Slots 520 provide additional attachment features for securing an instrument to receiver body 500. For example, one or both slots 520 may be configured to receive a tab or other extension on an instrument. Each slot 520 includes sidewalls 522 to limit rotational displacement of the instrument relative to the receiving body.

Figure 8:
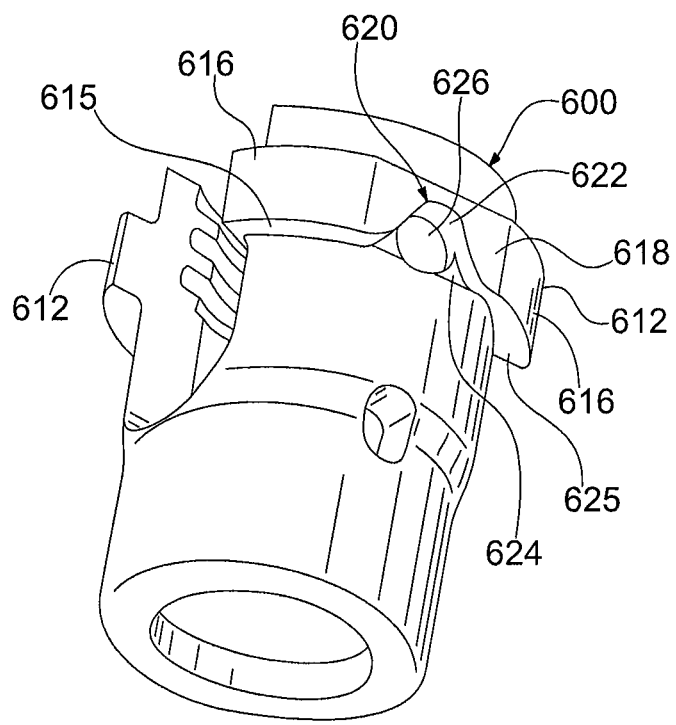
FIG. 8 is a perspective view of an alternate rod receiver in accordance with another exemplary embodiment of the present invention.

FIG. 8 shows a receiver body 600 with another flange configuration in accordance with the invention. Receiver body 600 includes flanges 612 with circular segments 616 and flat segments 618. Each flat segment 618 has a notch 620 with an inverted U-shaped pin receiving portion 622 and an apron portion 624. Pin receiving portion 622 includes a shallow bore 626. Apron portion 624 features a wider opening 625 adjacent the distal end 615 of flange 612. Flanges 612 provide an alternative attachment configuration for instrumentation that allows instruments to be twisted or rotated over the flanges to an axially-locked condition, as described in other embodiments above, or to apply upward axial force to the receiver body. Alternatively, flanges 612 provide attachment points for instruments to be pivotally attached to the receiver body.

Figure 9:
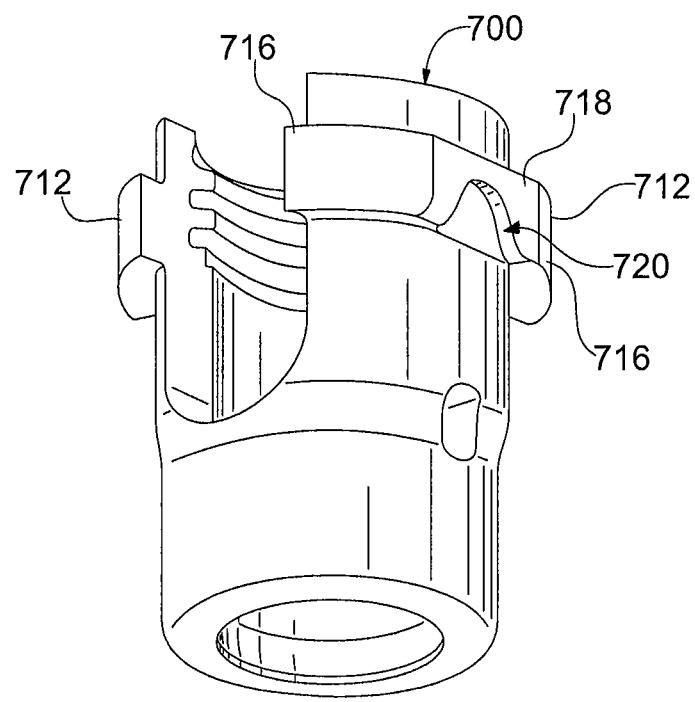
FIG. 9 is a perspective view of an alternate rod receiver in accordance with another exemplary embodiment of the present invention.
Figure 10:
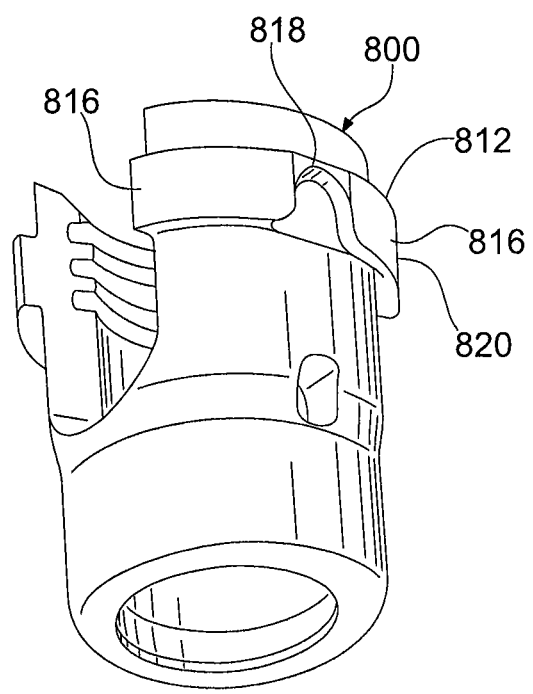
FIG. 10 is a perspective view of an alternate rod receiver in accordance with another exemplary embodiment of the present invention.

FIG. 9 shows another receiver body 700 with a flange configuration in accordance with the invention. Receiver body 700 includes flanges 712 with circular segments 716 and flat segments 718. Each flat segment 718 includes a notch 720 similar to notches 620 in receiver body 600, but with no shallow bore. FIG. 10 shows yet another receiver body 800 having flanges 812 with modified circular segments 816 and flat segments 818. Circular segments 816 occupy a larger portion of each flange's circumference, as compared with circular segments 716 on receiver body 700. Conversely, flat segments 818 make up a much smaller portion of each flange's circumference, as compared with flat segment 718 on receiver body 700. Flat segments 818 each feature a narrower notch opening 820.

Figure 11:
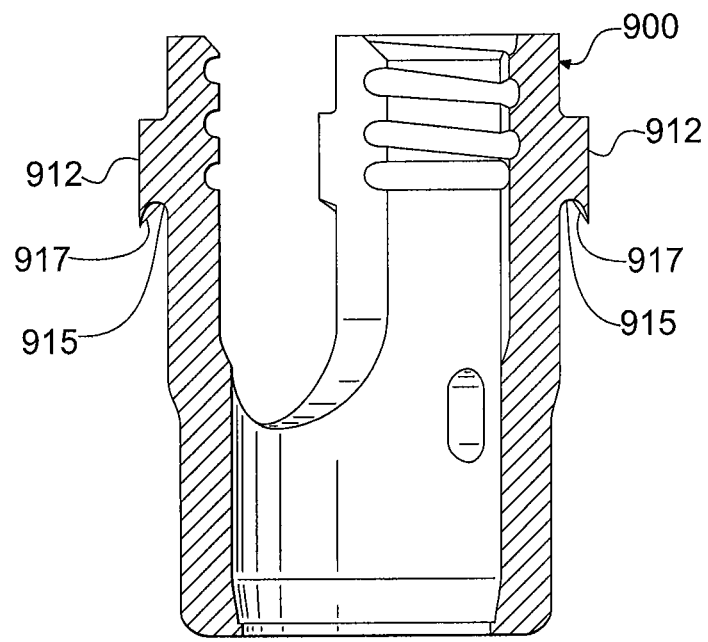
FIG. 11 is a cross-sectional view of an alternate rod receiver in accordance with another exemplary embodiment of the present invention.
Figure 12:
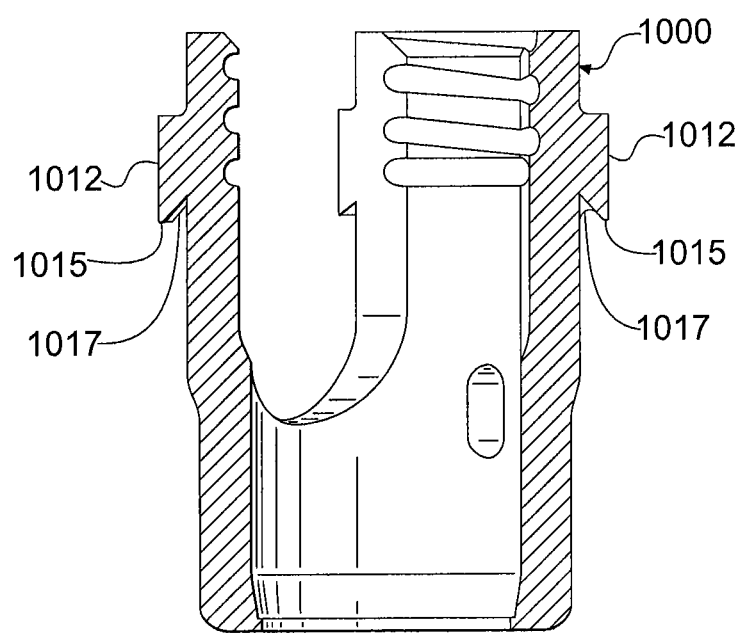
FIG. 12 is a cross-sectional view of an alternate rod receiver in accordance with another exemplary embodiment of the present invention.
Figure 13:
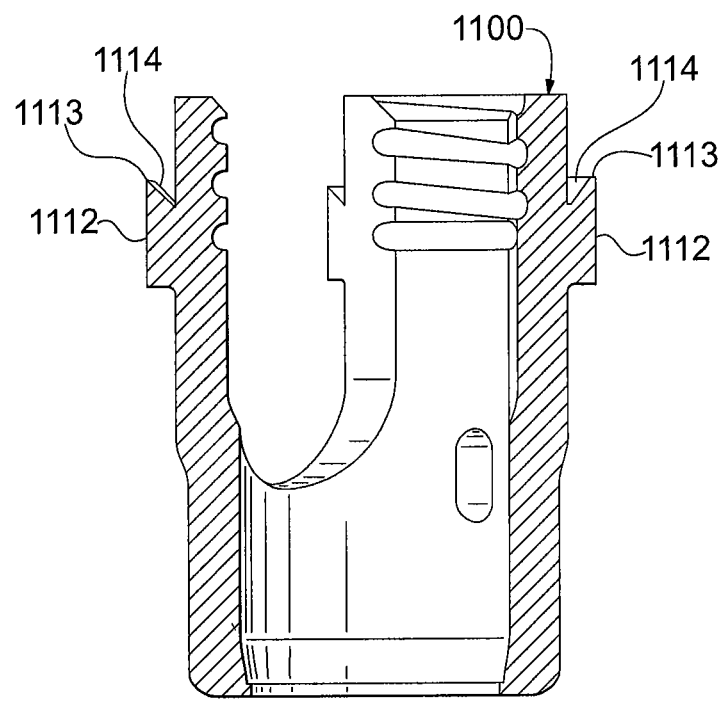
FIG. 13 is a cross-sectional view of an alternate rod receiver in accordance with another exemplary embodiment of the present invention.

FIGS. 11-13 show cross-sectional views of receiver bodies in accordance with the invention to illustrate optional flange profiles. FIG. 11 shows a receiver body 900 with a flange 912 having a distal edge 915 that forms a rounded channel 917. FIG. 12 shows a receiver body 1000 with a flange 1012 having a distal edge 1015 that forms a slanted or V-shaped channel 1017. Finally, FIG. 13 shows a receiver body 1100 with a flange 1112 having a proximal edge 1113 that forms a slanted or V-shaped channel 1114. Various flange profiles may be used on receiver bodies in accordance with the invention to mate with instrumentation, including but not limited to flange profiles having rectangular, circular, triangular or irregularly-shaped channels, notches, cutouts and protuberances.

Figure 14:
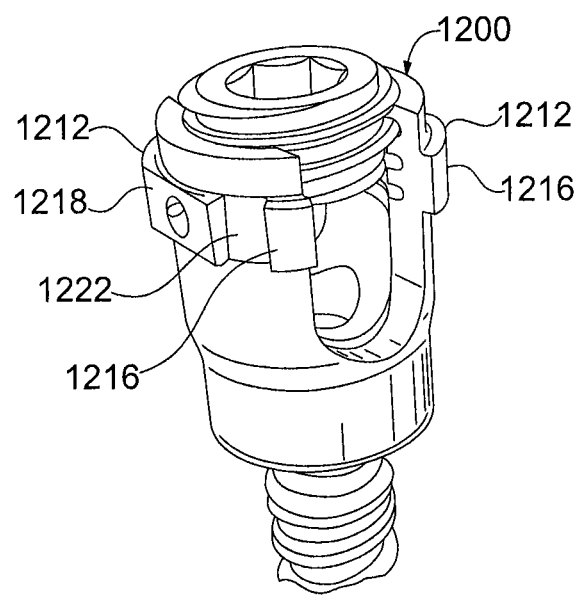
FIG. 14 is a perspective view of a spinal fixation construct, showing a rod receiver component in accordance with another exemplary embodiment of the present invention, with elements of the construct truncated for clarity.

FIG. 14 shows another construct with a receiver body 1200 with modified flanges 1212. Each flange 1212 includes two circular segments 1216 and a flat segment 1218 between the circular segments. Each flat segment 1218 includes a bore 1220, which serves as pivot attachment point for instruments. Unlike some of the other embodiments, receiver body 1200 provides a mechanism for locking the radial position of an instrument after the instrument's attachment members are passed over flat segments 1218, and rotated or "twisted" around beneath circular segments 1216. This is achieved by an axial cut-out or channel 1222 on one of the circular segments 1216. After an instrument is twisted over the circular segments 1216, a pin or other male protuberance on the instrument can be inserted or engaged with axial channel 1222 to lock the radial position of the instrument on the receiver body.

Figure 15:
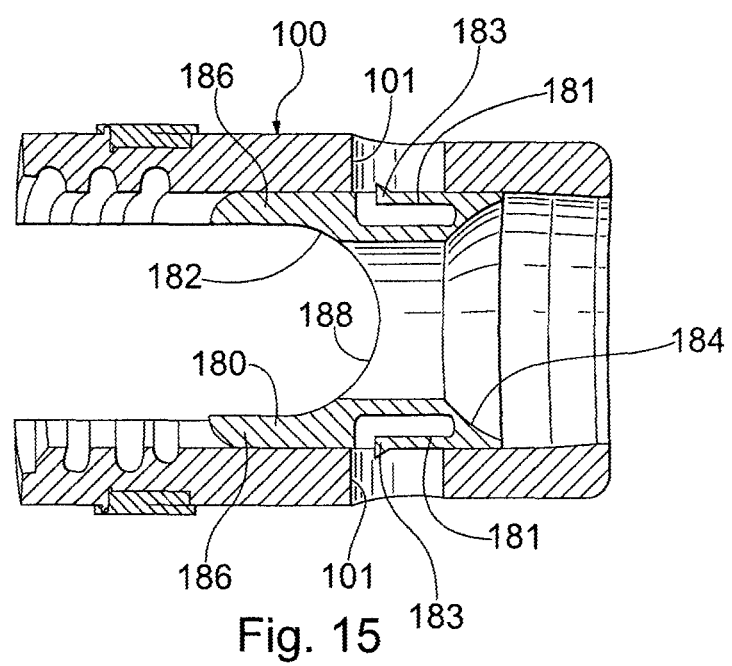
FIG. 15 is a cross-sectional view of the rod receiver of FIG. 2, showing an internal component in the rod receiver.

In preferred embodiments of the invention, the receiver body incorporates internal components to enhance and strengthen rod fixation. Referring now to FIG. 15, a cross-sectional view of receiver body 100 is shown. Receiver body 100 includes an insert 180. Insert 180 has a proximal saddle end 182 and a frusto-spherical distal end 184. Saddle end 182 has pair of tabs 186, each tab having a U-shaped slot 188 for receiving a rod. The frusto-spherical distal end 184 is configured to conform with and engage the spherical contour of a screw head. In this configuration, the insert ensures that both the rod and screw head are tightly secured in the rod receiver when the fixing element is tightened or locked down. When the fixing element is not tightened or locked down, the insert is unrestrained in the receiver body. To prevent insert 180 from backing out of receiver body 100, the insert includes a pair of flexible extensions 181 that align with and enter a pair of apertures 101. Each extension 181 has a locking tab 183. When insert 180 is inserted down into receiver body 180, locking tabs 183 are pressed inwardly by the sidewalls, which deflects the extensions 181 radially inwardly. Extensions 181 remain deflected until locking tabs 183 align with apertures 101. Once tabs 183 align with apertures 101, the tabs are no longer pressed inwardly by the sidewalls of the receiver body, allowing extensions 181 to snap radially outwardly. In this condition, tabs 183 engage the walls of apertures 101 to prevent insert 180 from being reversed out of receiver body 100. Insert 180 can be released and removed from receiver body by inserting small implements through the apertures 101 and pressing extensions 181 inwardly to move the tabs 183 out of the apertures.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A receiver body for an elongated spinal fixation element, the receiver body comprising:
   a housing portion having a first slot and a second slot opposite the first slot, the first and second slots forming a passage through the housing portion, the housing portion further comprising an outer wall;
   a first flange extending radially outwardly from the housing portion, the first flange having a circular perimeter edge extending radially outwardly from the outer wall in a cantilevered arrangement and a chamfered section extending radially outwardly from the outer wall in a cantilevered arrangement, the chamfered section having a notched undercut for engagement with an instrument; and
   a second flange extending radially outwardly from the housing portion oppositely arranged from the first flange, the second flange having a circular perimeter edge extending radially outwardly from the outer wall in a cantilevered arrangement and a chamfered section extending radially outwardly from the outer wall in a cantilevered arrangement, the chamfered section having a notched undercut for engagement with an instrument, the notched undercut of the second flange positioned diametrically opposite the notched undercut of the first flange.

2. The receiver body of claim 1, wherein an axis extending between the notched undercuts extends through the housing portion perpendicularly to the passage.

3. The receiver body of claim 1, wherein the notched undercuts each comprise a shallow bore extending into the housing portion.

4. The receiver body of claim 1, wherein the notched undercuts each comprise an inverted U-shaped engagement surface for an instrument.

5. The receiver body of claim 1, wherein the notched undercuts each comprise a shallow bore extending into the housing portion, and an inverted U-shaped engagement surface defining a portion of the perimeter of the shallow bore.

6. The receiver body of claim 1, wherein the notched undercuts each comprise an inverted U-shaped engagement surface for an instrument, and a flared opening adjacent the inverted U-shaped engagement surface.

7. The receiver body of claim 6, wherein the flared opening comprises a pair of rounded shoulders symmetrically arranged with respect to the U-shaped engagement surface, the shoulders forming guiding ramps that converge toward the U-shaped engagement surface to direct an instrument engagement feature into the U-shaped engagement surface.

8. The receiver body of claim 1, wherein the first and second flanges each comprise in instrument engagement means for slidable engagement with an instrument.

9. The receiver body of claim 8, wherein the instrument engagement means comprises a rounded channel extending circumferentially on distal edges of the first and second flanges.

10. The receiver body of claim 8, wherein the instrument engagement means comprises a channel extending circumferentially on proximal or distal edges of the first and second flanges.

11. A receiver body for an elongated spinal fixation element, the receiver body comprising a housing portion having an outer wall, the housing portion further comprising a circular flange extending radially outwardly from the outer wall in a cantilevered arrangement, the circular flange comprising a first chamfered section and a second chamfered section diametrically opposite the first chamfered section, the first and second chamfered sections extending radially outwardly from the outer wall in a cantilevered arrangement, the circular flange forming an engagement edge facing a distal end of the receiver body, the first chamfered section having a first aperture that opens out beneath the flange, and the second chamfered section having a second aperture that opens out beneath the flange, the first and second apertures forming diametrically opposed pivot-attachment points for an instrument.

12. The receiver body of claim 11, wherein an axis extending through the first and second apertures define an instrument pivot axis extending perpendicularly to a longitudinal axis passing through the housing body.

13. The receiver body of claim 11, wherein the apertures each comprise a shallow bore extending into the housing portion.

14. The receiver body of claim 11, wherein the apertures each comprise an inverted U-shaped engagement surface for an instrument.

15. The receiver body of claim 11, wherein the apertures each comprise a shallow bore extending into the housing portion, and an inverted U-shaped engagement surface defining a portion of the perimeter of the shallow bore.

16. The receiver body of claim 11, wherein the apertures each comprise an inverted U-shaped engagement surface for an instrument, and a flared opening adjacent the inverted U-shaped engagement surface.

17. The receiver body of claim 16, wherein the flared opening comprises a pair of rounded shoulders symmetrically arranged with respect to the U-shaped engagement surface, the shoulders forming guiding ramps that converge toward the U-shaped engagement surface to direct an instrument engagement feature into the U-shaped engagement surface.

18. The receiver body of claim 17, wherein the flange comprises an instrument engagement means extending circumferentially around the housing portion for slidable engagement with an instrument.

19. The receiver body of claim 18, wherein the instrument engagement means comprises a rounded channel extending circumferentially on the engagement edge of the flange.

20. The receiver body of claim 11, wherein the housing portion comprises a first slot and a second slot opposite the first slot, the first and second slots forming a passage through the housing portion between the diametrically-opposed pivot-attachment points.

21. The receiver body of claim 1, wherein the first flange comprises a first arc-shaped section on a first side of the chamfered section, and a second arc-shaped section on a second side of the chamfered section opposite the first side of the chamfered section, the first and second arc-shaped sections symmetrically arranged on the first and second sides of the chamfered section.

22. The receiver body of claim 11, wherein the circular flange comprises a first arc-shaped section on a first side of the first chamfered section, and a second arc-shaped section on a second side of the first chamfered section opposite the first side of the first chamfered section, the first and second arc-shaped sections symmetrically arranged on the first and second sides of the first chamfered section.

23. A receiver body for an elongated spinal fixation element, the receiver body comprising:
  a housing portion having a first slot and a second slot opposite the first slot, the first and second slots forming a passage through the housing portion, the housing portion further comprising an outer wall;
  a first flange extending radially outwardly from the housing portion, the first flange having a circular perimeter edge extending radially outwardly from the outer wall in a cantilevered arrangement and a flattened section extending radially outwardly from the outer wall in a cantilevered arrangement, the circular perimeter edge comprising a first arc-shaped section on a first side of the flattened section and a second arc-shaped section on a second side of the flattened section, the flattened section having a notched undercut for engagement with an instrument; and
  a second flange extending radially outwardly from the housing portion, the second flange having a circular perimeter edge extending radially outwardly from the outer wall in a cantilevered arrangement and a flattened section extending radially outwardly from the outer wall in a cantilevered arrangement, the circular perimeter edge of the second flange comprising a first arc-shaped section on a first side of the flattened section of the second flange, and a second arc-shaped section on a second side of the flattened section of the second flange, the flattened section of the second flange having a notched undercut for engagement with an instrument.

* * * * *